United States Patent [19]

Findeisen et al.

[11] Patent Number: 4,504,673

[45] Date of Patent: Mar. 12, 1985

[54] PREPARATION OF TARTRONIC ESTERS

[75] Inventors: Kurt Findeisen, Odenthal; Rudolf Fauss, Cologne, both of Fed. Rep. of Germany

[73] Assignee: Bayer Aktiengesellschaft, Leverkusen, Fed. Rep. of Germany

[21] Appl. No.: 599,038

[22] Filed: Apr. 11, 1984

[30] Foreign Application Priority Data

May 4, 1983 [DE] Fed. Rep. of Germany ....... 3316264

[51] Int. Cl.³ ............................................ C07C 69/675
[52] U.S. Cl. ..................................... 560/180; 556/417
[58] Field of Search ................ 560/180, 190; 556/417; 260/465.8 R

[56] References Cited

U.S. PATENT DOCUMENTS 2,843,603  7/1958  Stork ..................................... 560/190
3,567,749  3/1971  Neugebauer et al. ............... 560/190
3,720,679  3/1973  Feldman et al. ............. 260/465.8 R
3,997,593 12/1976  Stadler et al. ........................ 560/180

FOREIGN PATENT DOCUMENTS 0056264 7/1982 European Pat. Off. .

OTHER PUBLICATIONS

Lidy et al., *Chemical Abstracts*, 78:111408, (1973).
Mukherji, "Preparation of Triethyl 2–methyl–5–isopropylpentane–1,2,5–tricarboxylate," *J. Ind. Chem. Soc.*, vol. 40, No. 5, pp. 405–406, (1963).
Migrdichian, *Organic Synthesis*, vol. 1, Reinhold Publishing Corp., New York, pp. 429–430, (1957).

*Primary Examiner*—Natalie Trousof
*Assistant Examiner*—Bruce D. Gray
*Attorney, Agent, or Firm*—Sprung, Horn, Kramer & Woods

[57] ABSTRACT

A process for the preparation of a tartronic ester of the formula

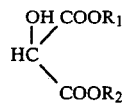

in which $R_1$ and $R_2$ each independently is an optionally substituted alkyl or cycloalkyl radical, comprising reacting (trimethylsilyloxy)tricyanomethane in the presence of a mineral acid, with at least one alcohol of the formula $R_1OH$ and $R_2OH$ and hydrolyzing the product of reaction. Advantageously the alcohols are employed in at least three times the molar amount of the (trimethylsilyloxy)tricyanomethane, and the reaction and hydrolysis are carried out in immediate succession in the same reaction vessel.

8 Claims, No Drawings

PREPARATION OF TARTRONIC ESTERS

The invention relates to a new process for the preparation of alkyl and cycloalkyl tartronates.

Alkyl tartronates, for example methyl and ethyl tartronates, have hitherto been obtained by reacting the sodium, calcium or barium salts of tartronic acid with the appropriate anhydrous alcohol containing hydrogen chloride (see the details in Beilsteins Handbuch der Organischen Chemie (Beilstein's Handbook of Organic Chemistry) volume 3, page 416, 1st supplement page 148, 2nd supplement page 274.

However, because of the difficulty of obtaining tartronic acid, this reaction does not represent an actual process for preparation but merely a manner of formation. However, since tartronic esters have found practical use as starting compounds for the preparation of fungicides of the N-aryl-1,3-oxazolidin-2,4-dione series (see DE-OS No. (German Published Specification) 2,906,574), the industrial object was to discover a straightforward and economical process for preparing tartronic esters.

It has been found according to the invention that alkyl and cycloalkyl tartronates of the formula

are obtained in a straightforward and economical manner when trimethylsilyloxytricyanomethane of the formula

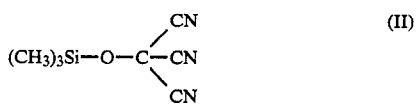

is used as starting material and, in a two-stage reaction, is first reacted with alcohols of the formula $R_1OH$ and $R_2OH$, in the presence of mineral acids, and then the product of reaction is hydrolyzed. It has been found, surprisingly, that the Pinner reaction of trimethylsilyloxytricyanomethane does not lead, as was to be expected, to conversion of all CN groups into COOR groups, but, when the Pinner reaction is applied to trimethylsilyloxy-tricyanomethane, one of the CN groups is replaced by hydrogen.

Thus, the invention relates to a process for the preparation of tartronic esters of the formula

in which $R_1$ and $R_2$, independently of one another, represent an optionally substituted alkyl or cycloalkyl radical, which is characterized by reacting (trimethylsilyloxy)tricyanomethane with alcohols of the formula $R_1OH$ and $R_2OH$ in the presence of mineral acids, and hydrolyzing the product of reaction.

Esters of the formula (I) in which $R_1$ and $R_2$, independently of one another, represent a $C_1$-$C_8$-alkyl or a $C_3$-$C_6$-cycloalkyl radical are preferred.

The process according to the invention also makes it possible to prepare alkyl and cycloalkyl tartronates of the formula (I), the alkyl and cycloalkyl radicals $R_1$ and $R_2$ of which are substituted by, for example, halogen atoms, in particular fluorine, chlorine and bromine atoms, $C_1$-$C_4$-alkyl radicals, $C_1$-$C_4$-alkoxy, radicals, for example the methoxy or the ethoxy radical and/or phenyl or phenoxy radicals. Examples of these types of substituted alkyl radicals are, for example, the 2-fluoro-, 2-methoxy-, 2-ethoxy- and 2-phenoxyethyl radical, also the methyl- and the tert.-butylcyclohexyl radical.

$R_1$ and $R_2$ preferably represent the methyl, ethyl, n-propyl and isopropyl radical.

The (trimethylsilyloxy)tricyanomethane to be used as starting compound according to the invention is known and is obtained by reaction of phosgene with trimethylsilyl cyanide (see Angewandte Chemie 94, 4 (1982)).

In carrying out the process according to the invention, it is unnecesary to isolate the product of reaction produced in the reaction of the (trimethylsilyloxy)tricyanomethane with the alcohols in the presence of the mineral acids. On the contrary, the reaction and the hydrolysis are, preferably, carried out in immediate succession in one and the same reaction vessel.

3 mols of alcohol and 3 equivalents of mineral acid per mol of (trimethylsilyloxy)tricyanomethane are required for the reaction of the (trimethylsilyloxy)tricyanomethane. However, it is advantageous to use an excess of alcohol, for example 4 to 20 mols of alcohol per mol of (trimethylsilyloxy)tricyanomethane; the excess alcohol serves at the same time as the diluent. It is also possible to use, in place of excess alcohol, organic diluents which are inert under the reaction conditions, for example hydrocarbons, such as benzene and toluene, or halogenated hydrocarbons, such as methylene chloride, dichloroethane and chlorobenzene, or sulpholane.

The mineral acids which are particularly used are sulphuric acid, phosphoric acid and perchloric acid and, preferably, hydrogen chloride.

The reaction according to the invention of trimethylsilyloxy)tricyanomethane with the alcohols in the presence of the mineral acids is carried out at temperatures of $-10°$ to $60°$ C., preferably of $10°$ to $40°$ C. In order to complete the reaction, the reaction mixture is subsequently stirred at temperatures of $20°$ to $80°$ C., and then an amount of water is added such that at least 3 mols of water is present to 1 mol of (trimethylsilyloxy)tricyanomethane. Exceeding this stoichiometrically necessary amount of water has no adverse effects. After the addition of water, the reaction mixture is stirred at temperatures from $20°$ C. to the boiling point of the reaction mixture and then worked up in a manner known per se. The working up of the reaction mixture can be carried out directly by distillation; with this procedure, the precipitated ammonium chloride is advantageously first removed by filtration. However, the working up can also be carried out in a manner such that the reaction mixture is first discharged onto ice(-water) and the ester is removed from the aqueous phase by extraction with a solvent which is essentially insoluble in water, for example methylene chloride, methyl acetate, toluene or chlorobenzene, and work-up by distillation is only carried out on the extract. Esterification using hydrochloric acid and direct working up by distillation are preferably used. The O-substituted urethane, which is produced in minor amounts as a by-product of the reaction, can be removed from the desired tartronic ester by distillation.

The reaction according to the invention of (trimethylsilyloxy)tricyanomethane with alcohols in the presence of mineral acids is preferably carried out in such a manner that the alcohol and the inorganic acid are initially introduced, and the (trimethylsilyloxy)tricyanomethane is introduced with stirring. However, the reaction can also be carried out in a manner such that the (trimethylsilyloxy)tricyanomethane is initially added to the mineral acid and then the anhydrous alcohol is added. If the reaction is carried out using only one alcohol, then tartronic esters containing the same ester radicals are obtained. To prepare mixed tartronic esters, mixtures of the alcohols forming the ester groups are employed. The best procedure has proved to be that in which the anhydrous alcohol is saturated with hydrogen chloride gas, and (trimethylsilyloxy)tricyanomethane is introduced into this alcohol containing hydrochloric acid.

EXAMPLE 1

1,800 ml of absolute ethanol is saturated with HCl gas at room temperature and then, at a maximum of 30° C., first 537 g (trimethylsilyloxy)tricyanomethane are added dropwise and, after stirring for 30 minutes, 54 g of water are added dropwise. After heating at the reflux temperature for 1 hour, followed by cooling, the $NH_4Cl$ is filtered off with suction and the filtrate is concentrated in vacuo. The liquid residue is distilled in vacuo (over a 1 meter long Vigreux column).

316 g (55% of theory) of diethyl tartronate of boiling point 111°–113° C./16 mbar are obtained.

EXAMPLE 2

300 ml of anhydrous ethanol are saturated with HCl gas at 10° C. and then, at 0° C., 102 g of (trimethylsilyloxy)tricyanomethane are added. The mixture is then stirred at 15° C. for 1 hour and subsequently diluted with 300 ml of water. After stirring for 30 minutes, ice-water is added and the mixture is extracted with methylene chloride. Working up the methylene chloride extract and vacuum distillation of the residue provides 86 g (50% of theory) of diethyl tartronate of boiling point 112°–113° C./16 mbar.

EXAMPLE 3

44 g of (trimethylsilyloxy)tricyanomethane are added dropwise, with stirring, to a mixture of 200 g of sulphuric acid (100% strength) and 50 g of methanol at 30° C. The temperature is maintained at 50° to 60° C. during the addition. Then a mixture of 13.5 g of water and 50 ml of methanol are added to the reaction mixture and it is stirred for a further 1 hour at 40° C. The reaction mixture is poured onto ice and extracted several times with methylene chloride. The combined methylene chloride extracts are washed once with a little water and then concentrated. On distillation of the crude product, 10 g (31% of theory) of dimethyl tartronate of boiling point 112° C./20 mbar, melting point: 55° C., are obtained.

It will be understood that the specification and examples are illustrative but not limitative of the present invention and that other embodiments within the spirit and scope of the invention will suggest themselves to those skilled in the art.

We claim:

1. A process for the preparation of a tartronic ester of the formula

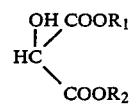

in which $R_1$ and $R_2$ each independently in an optionally substituted alkyl or cycloalkyl radical, comprising reacting (trimethylsilyloxy)tricyanomethane in the presence of a mineral acid, with at least one alcohol of the formula $R_1OH$ and $R_2OH$ and hydrolyzing the product of reaction.

2. A process according to claim 1, wherein the alcohols $R_1OH$ and/or $R_2OH$ are employed in at least three times the molar amount of the (trimethylsilyloxy)tricyanomethane.

3. A process according to claim 1, wherein the reaction with the (trimethylsilyloxy)tricyanomethane is carried out in a diluent.

4. A process according to claim 3, wherein excess alcohol $R_1OH$ and/or $R_2OH$ is used as the diluent.

5. A process according to claim 1, wherein the reaction with the (trimethylsilyloxy)tricyanomethane is carried out at a temperature from about $-10°$ to 60° C.

6. A process according to claim 1, wherein the reaction of the (trimethylsilyloxy)tricyanomethane with the alcohols in the presence of a mineral acid, and the subsequent hydrolysis are carried out in immediate succession in the same reaction vessel.

7. A process according to claim 1, in which $R_1$ and $R_2$ each independently is $C_1$–$C_8$-alkyl/or $C_3$–$C_6$-cycloalkyl each optionally and independently substituted by halogen, $C_1$–$C_4$-alkyl, $C_1$–$C_4$-alkoxy, phenyl or phenoxy.

8. A process according to claim 7, wherein the reaction of the (trimethylsilyloxy)tricyanomethane with the alcohols in the presence of a mineral acid, and the subsequent hydrolysis are carried out in immediate succession in the same reaction vessel, the alcohols $R_1OH$ and/or $R_2OH$ being employed in at least three times the molar amount of the (trimethylsilyloxy)tricyanomethane.

* * * * *